US011793949B2

(12) United States Patent
Adelaar et al.

(10) Patent No.: US 11,793,949 B2
(45) Date of Patent: Oct. 24, 2023

(54) SECURE ELECTRONIC VAPORIZER AND NEBULIZER SYSTEMS

(71) Applicant: Jesse David Adelaar, New York, NY (US)

(72) Inventors: Jesse David Adelaar, New York, NY (US); David Matthias Bowman, Ponte Vedra, FL (US)

(*) Notice: Subject to any disclaimer, the term of this patent is extended or adjusted under 35 U.S.C. 154(b) by 597 days.

(21) Appl. No.: 16/927,639

(22) Filed: Jul. 13, 2020

(65) Prior Publication Data

US 2021/0093805 A1    Apr. 1, 2021

Related U.S. Application Data

(63) Continuation of application No. 16/584,793, filed on Sep. 26, 2019, now Pat. No. 10,737,041.

(51) Int. Cl.
*A61M 11/04* (2006.01)
*A61M 16/16* (2006.01)
*A61M 16/10* (2006.01)

(52) U.S. Cl.
CPC ........ *A61M 11/042* (2014.02); *A61M 16/109* (2014.02); *A61M 16/16* (2013.01);
(Continued)

(58) Field of Classification Search
CPC .......... A61M 16/16; A61M 16/18–186; A61M 2205/3375; A61M 2205/50; A61M 2205/8206; A61M 11/005; A61M 11/02; A61M 15/0081; A61M 15/0003; A61M 15/06; A61M 15/0066; A61M 2016/0021; A61M 2016/0033; A61M 2202/0241; A61M 2202/0468; A61M 2205/18; A61M 2205/27; A61M 2205/276; A61M 2205/3306; A61M 2205/3317; A61M 2205/3368; A61M 2205/3379;
(Continued)

(56) References Cited

U.S. PATENT DOCUMENTS 3,443,726 A    5/1969 Godsted
8,381,739 B2    2/2013 Gonda
(Continued)

FOREIGN PATENT DOCUMENTS

CN    108771290 A    11/2018

OTHER PUBLICATIONS

PCT International Search Report and Written Opinion dated Jan. 27, 2021 regarding International Application No. PCT/US2020/049119, 16 pages.

*Primary Examiner* — Elliot S Ruddie
(74) *Attorney, Agent, or Firm* — Knobbe, Martens, Olson & Bear LLP

(57) ABSTRACT

Methods and systems are described herein for fluid handling and dispensing liquid substances using vaporization or nebulization in a controlled, safe manner. A dispensing device may be configured to receive one or more cartridges storing different types of vaporizable or nebulizable substances. A controller may be provided to regulate the amount of a given substance dispensed over a defined time period. Optionally, in response to detecting tampering of the dispensing device and/or a liquid cartridge the dispensing device may be disabled and/or a liquid stored in a substance cartridge may be rendered inert.

26 Claims, 7 Drawing Sheets

(52) U.S. Cl.
CPC . *A61M 2205/3375* (2013.01); *A61M 2205/50* (2013.01); *A61M 2205/8206* (2013.01)

(58) Field of Classification Search
CPC .. A61M 2205/3553; A61M 2205/3569; A61M 2205/3592; A61M 2205/505; A61M 2205/6018; A61M 2205/609; A61M 2209/01; A61M 2230/20; A61M 11/04–042; A61M 15/0021; A61M 2205/3372; A61M 2205/3653; A61M 2205/368; G16H 20/13; A24F 40/50; A24F 40/65; A24F 40/10; A24F 47/00; A24F 47/002; A24F 47/004; A24F 47/008; A61K 9/007; A61K 9/0073; A61K 9/0078; A61K 47/44
USPC ............ 128/200.24; 131/194, 273, 299, 300, 131/309, 310, 329, 900, 901, 902, 903
See application file for complete search history.

(56) References Cited

U.S. PATENT DOCUMENTS

| | | |
|---|---|---|
| 9,839,241 B2 | 12/2017 | Davidson et al. |
| 2003/0052196 A1* | 3/2003 | Fuchs ................ A61M 15/008 239/338 |
| 2004/0084044 A1* | 5/2004 | Childers ............. A61M 15/025 128/200.14 |
| 2006/0130828 A1 | 6/2006 | Sexton |
| 2006/0157491 A1* | 7/2006 | Whittle ............... G07F 17/0092 221/9 |
| 2008/0023497 A1* | 1/2008 | Sassoon .................... A61L 2/22 222/402.11 |
| 2011/0265806 A1 | 11/2011 | Alarcon et al. |
| 2011/0277757 A1 | 11/2011 | Terry et al. |
| 2012/0227752 A1 | 9/2012 | Alelov |
| 2012/0291791 A1 | 11/2012 | Pradeep |
| 2013/0220315 A1 | 8/2013 | Conley et al. |
| 2013/0319439 A1 | 12/2013 | Gorelick et al. |
| 2016/0089508 A1* | 3/2016 | Smith ............... A61M 15/0085 128/202.21 |
| 2016/0106936 A1 | 4/2016 | Kimmel |
| 2016/0206610 A1 | 7/2016 | Armer |
| 2017/0251721 A1 | 9/2017 | Rostami et al. |
| 2017/0258138 A1 | 9/2017 | Rostami et al. |
| 2017/0279830 A1* | 9/2017 | Mermoud .......... A61M 15/009 |
| 2018/0060527 A1 | 3/2018 | Kalyanpur |
| 2018/0110939 A1* | 4/2018 | Lanzkowsky ........ A61K 31/675 |
| 2018/0296778 A1 | 10/2018 | Hacker |
| 2018/0368474 A1 | 12/2018 | Bache et al. |
| 2019/0125256 A1* | 5/2019 | Hays ........................ A61B 5/11 |

* cited by examiner

SECURE ELECTRONIC VAPORIZER AND NEBULIZER SYSTEMS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

This document relates to systems and techniques for fluid handling and dispensing liquid substances using vaporization or nebulization.

Description of the Related Art

Substance abuse and addiction are becoming ever more prevalent. Although techniques and devices have been developed, such conventional techniques have been inadequate in addressing substance abuse and addiction.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

An aspect of the present disclosure relates to methods and systems for fluid handling and dispensing liquid substances using vaporization or nebulization in a controlled, safe manner. A dispensing device may be configured to receive one or more cartridges storing different types of vaporizable or nebulizable substances. A controller may be provided to regulate the amount of vaporizable and/or nebulizable substances dispensed over a defined time period. Optionally, in response to detecting tampering of the dispensing device and/or a liquid container the dispensing device may be disabled and/or a liquid stored in a substance container may be rendered inert.

An aspect of the present disclosure relates to methods and systems that optionally enable the controlled, safe dispensing of vaporizable liquid substances, such as controlled substances and placebos. Optionally, in response to detecting tampering of a substance dispensing device and/or a substance container (e.g., a cartridge or other reservoir), the substance dispensing device may be disabled and/or a substance stored in a substance container may be rendered inert. Methods and systems are described that enable a detoxification plan and/or a controlled substance maintenance plan to be implemented.

An aspect of the present disclosure relates to an electronic personal vaporizer system, comprising: a first receiving area configured to removably receive a first cartridge including a vaporizable controlled substance; a second receiving area configured to removably receive a second cartridge including a vaporizable placebo substance; an inhalation sensor; a rechargeable battery; a network interface configured to be powered by the rechargeable battery; at least one computing device configured to be powered by the rechargeable battery; computer readable memory including instructions operable to be executed by the at least one computing device to perform a set of actions, configuring the at least one computing device to at least: store dispensing plan scheduling rules for the vaporizable controlled substance and the vaporizable placebo substance in the computer readable memory; at least partly in response to the inhalation sensor detecting a user inhalation, access the dispensing plan scheduling rules for: the vaporizable controlled substance, and the vaporizable placebo substance; access current date and current time data; access vaporizable controlled substance dispensing-related data for a first historical time period; based at least in part on: the dispensing plan scheduling rules for the vaporizable controlled substance and the vaporizable placebo substance, the accessed current date and current time data, and the vaporizable controlled substance dispensing-related data for the first historical time period, cause: a first amount of the vaporizable controlled substance to be dispensed from the first cartridge, a second amount of the vaporizable placebo substance to be dispensed from the second cartridge.

An aspect of the present disclosure relates to a computer implemented method executed using a substance dispensing system comprising: under control of a hardware computing device configured with specific computer executable instructions: receiving dispensing plan scheduling rules for a vaporizable or nebulizable controlled substance to be dispensed by the substance dispensing system; storing the dispensing plan scheduling rules for the vaporizable or nebulizable controlled substance in computer readable memory; detecting, using an inhalation sensor, a user inhalation; at least partly in response to the inhalation sensor detecting the user inhalation, accessing the dispensing plan scheduling rules for the vaporizable or nebulizable controlled substance; accessing current date and current time data; accessing vaporizable or nebulizable controlled substance dispensing-related data for a first historical time period; based at least in part on: the dispensing plan scheduling rules for the vaporizable or nebulizable controlled substance, the accessed current date and current time data, and the vaporizable or nebulizable controlled substance dispensing-related data for the first time historical period, enabling: a first amount of the vaporizable or nebulizable controlled substance to be dispensed from a first reservoir, a second amount of a vaporizable or nebulizable placebo substance to be dispensed from a second reservoir.

An aspect of the present disclosure relates to a non-transitory computer-readable storage medium storing computer executable instructions that when executed by a processor cause the processor to perform operations comprising: receiving a dispensing plan for a vaporizable or nebulizable controlled substance; storing the dispensing plan for the vaporizable or nebulizable controlled substance in computer readable memory; detecting, using a substance dispensing apparatus inhalation sensor, a user inhalation; at least partly in response to the inhalation sensor detecting the user inhalation, accessing the dispensing plan for the vaporizable or nebulizable controlled substance; accessing current date and current time data; accessing vaporizable or nebulizable controlled substance dispensing-related data for a first historical time period; based at least in part on: the dispensing plan for the vaporizable or nebulizable controlled substance, the accessed current date and current time data, and the vaporizable or nebulizable controlled substance dispensing-related data for the first time historical period, enabling: a first amount of the vaporizable or nebulizable controlled substance to be dispensed from a first reservoir, a second amount of a vaporizable or nebulizable placebo substance to be dispensed from a second reservoir.

BRIEF DESCRIPTION OF THE DRAWINGS

Embodiments will now be described with reference to the drawings summarized below. These drawings and the associated description are provided to illustrate example aspects of the disclosure, and not to limit the scope of the invention.

DETAILED DESCRIPTION

Figure 1:
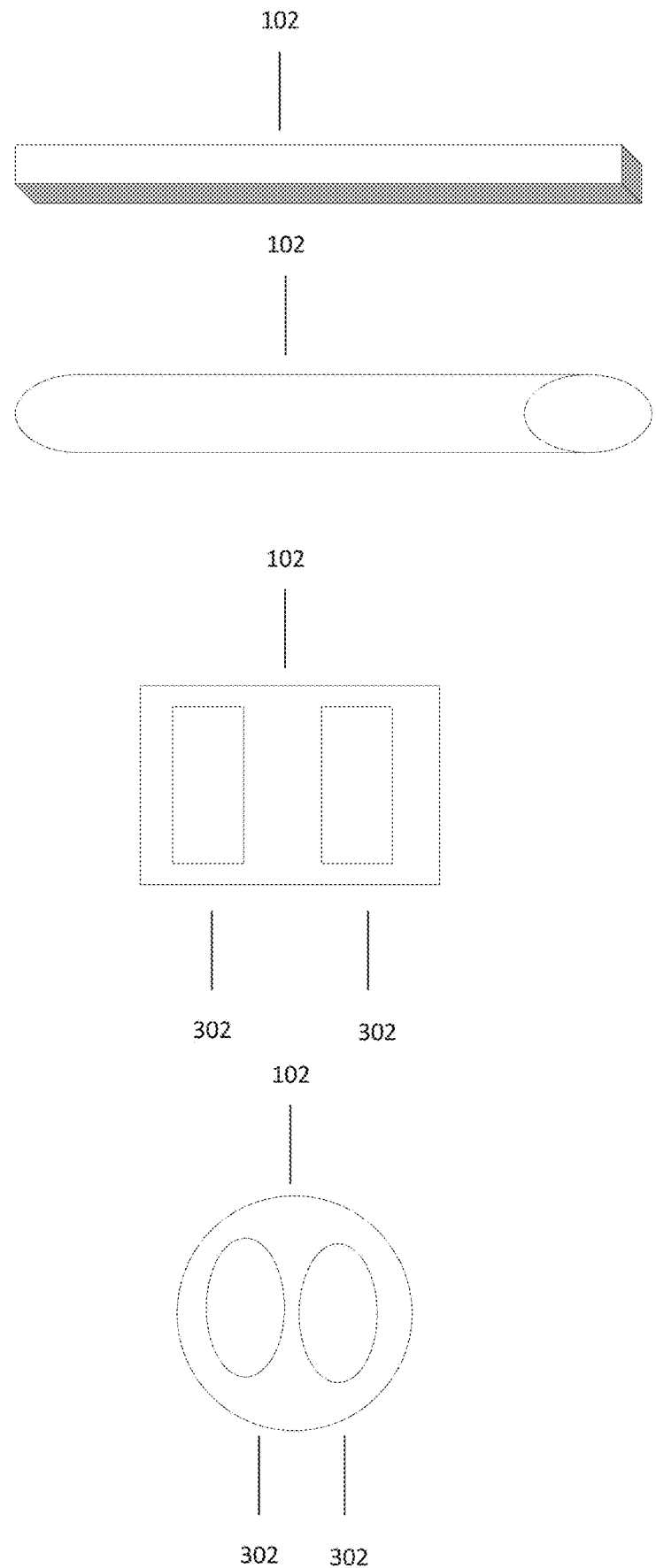
FIG. 1 illustrates an example substance dispensing device.

Illustrative substance dispensing devices and components are described herein. Systems and techniques for fluid handling and dispensing liquid substances using vaporization or nebulization are further described.

An example substance dispensing device may optionally be configured to receive multiple cartridges containing different substances (e.g., vaporizable materials). For example, one cartridge may store one type of substance (e.g., a controlled substance, such as a narcotic or prescribed pharmaceutical) and another cartridge may store a different substance (e.g., a placebo). For example, one or more receiving orifices and/or connectors may be provided in the substance dispensing device to receive respective cartridges. The substance dispensing device may optionally be configured to receive one or more multi-chamber cartridges, wherein one chamber may store one type of substance (e.g., a controlled substance, such as a narcotic) and another chamber may store a different substance (e.g., a placebo). The substance dispensing device may optionally be configured to receive a single cartridge storing a single substance. The substance dispensing device may be configured to selectively dispense liquid substances stored in one or more of the cartridges via nebulization. Thus, using one or more of the techniques described herein, one or more reservoirs may be provided to store a first type of vaporizable substance, and one or more reservoirs may be provided to store a second type of vaporizable substance, where the reservoirs may be housed in a single cartridge or via different cartridges.

The substance dispensing device may optionally be configured to be handheld and to be sized similar to that of a cigarette, cigar, or conventional "vape" device. The substance dispensing device may be configured to enable personal inhalation of the substances dispensed by the substance dispensing device. The substance dispensing device may include a rechargeable battery configured to power internal circuitry, one or more heating components that may include heating elements (e.g., resistive heating elements), and the nebulizer.

Optionally, the heating component may comprise a heater chamber, a substance wick, and a resistive heating element in contact with the substance wick. For example, the substance wick may be configured to contact/be immersed at least partly in the vaporizable substance stored in the cartridge, and draw the vaporizable substance towards or to the resistive heating element. A given heating element may be configured to heat viscous vaporizable substances stored in the cartridges to thereby generate a relatively low-temperature inhalable vapor.

Optionally, a given cartridge may include its own heating component which may be powered by the substance dispensing device rechargeable battery (e.g., via cartridge contacts that mate with substance dispensing device contacts). Optionally, the heating component may be included in the substance dispensing device. Optionally, a portion of the heating component may be included in the substance dispensing device and a portion of the heating component may be included in the cartridge. For example, the substance dispensing device may include the heating chamber and heating element, while the cartridge may include the substance wick.

One or more temperature sensors (included in the cartridge and/or the substance dispensing device) may be utilized to sense and control the temperature of a given heating element to ensure that the substances are vaporized and dispensed at a pleasurable temperature and ensure that the substance's chemistry is not altered or destroyed.

The cartridges and substance dispensing device may be configured so that the cartridges are easily removable and replaceable. Optionally, certain cartridges may be configured to be tamper resistant, wherein attempts to tamper with a cartridge and/or the substance dispensing device may destroy or alter substances contained within the cartridge (e.g., to reduce or eliminate a narcotic property of the substance). For example, in response to tampering, activated carbon or naloxone may be dispersed in the substance to render it inert (e.g., so that it does not provide a narcotic effect) while still being safe to consume. Optionally, certain cartridges (e.g., those containing a controlled substance) may be configured to be tamper resistant, while other cartridges (e.g., those containing a placebo) may not be configured to be tamper resistant.

Optionally, a given cartridge may include a computer readable memory storing some or all of the following information: an indication regarding the cartridge contents, the manufacturing date, lot number, a cartridge expiration date, a patient identifier, serial number, and/or a substance dispensing device unique identifier (indicating that the cartridge is only to be used with the substance dispensing device corresponding to the identifier). Optionally, the substance dispensing device may be configured not to dispense the contents of certain cartridges (e.g., that indicate they contain a controlled substance) if the substance dispensing device unique identifier stored in the cartridge does not match the identifier of the substance dispensing device into which the cartridge is inserted.

As will be described, a substance dispensing device may include a wireless interface (e.g., WiFi, a peer-to-peer interface such as WiFi Direct, Bluetooth, a low power interface, such as Bluetooth Low-Energy, ZigBee, Z-Wave, 6LoW-PAN, a cellular network interface such as a 3G, 4, 5G interface, and/or other interfaces). A given wireless interface may be coupled to an antenna. The substance dispensing device may be wirelessly paired with and/or communicate with a remote device (via an application installed on the device, such as a substance dispensing programming application), where the device may also be configured to prevent a user from improperly accessing a substance stored in a cartridge. For example, if the substance dispensing device does not receive a periodic message from the remote device (e.g., a heartbeat signal transmitted every 15 seconds, 30 seconds, 5 minutes, or other time period), the substance dispensing device may cease dispensing a substance stored in one or more (e.g., all) the cartridges installed on the substance dispensing device.

Optionally, in response to detecting an attempt to tamper with the substance dispensing device (where the hacking is performed on the substance dispensing device hardware or the substance dispensing device software), the substance dispensing device may automatically be permanently disabled or temporarily disabled (where an authorized entity may re-enable the device) so that the substance dispensing device is unable to dispense any drug/controlled substance and is optionally unable to dispense the placebo substance as well. For example, a semiconductor fuse included in a processing device or heater control element may be blown to prevent powering of heating elements. For example, software hacking (e.g., a DNS rebinding attack, a denial service attack, attempted insertions of malware) may be detected by monitoring the content and/or source of data packets being transmitted to and/or from the substance dispensing device and/or to a device (e.g., a smart phone) having an application thereon configured to manage the substance dispensing device.

Optionally, a remote administrator (e.g., a physician, an addiction specialist, or other unauthorized person) can remotely monitor patient misuse or tampering of the substance dispensing device, or non-compliance with a detoxification plan. In response to detecting non-compliance or tampering, the administrator may temporarily or permanently disable the substance dispensing device via a user interface provided via an application hosed on a remote administrator or via a webpage hosted by a web server By way of example, the substance dispensing device may optionally be configured to dispense medications or drugs, such as an opiate or other psychotropic drug (e.g., available in liquid formulations, such as fluoxetine, paroxetine, citalopram, GHB, etc.), so as to aid a user in managing an addiction and/or as part of a detoxification process.

By way of illustration, the substance dispensing device may be configured to provide regulation of the intake of potentially addictive substance under prescription to curtail abuse and/or to taper intake of an addictive substance as part of a detoxification process. The substance dispensing device may include a controller device (e.g., a microprocessor, a microcontroller, a state machine, and/or the like) configured to be programmed (e.g., via a user device, such as a smart phone or other device with a substance dispensing programming application installed thereon) to control the amount of substance from a give cartridge to be dispensed per inhalation or for a given time period. Such control enables drug output to be precisely regulated to a desired rate and total amounts.

Optionally, as discussed above, the substance dispensing device may be configured to receive a single cartridge or multiple cartridges where each cartridge stores the same substance. Optionally, the substance dispensing device may be configured to receive at least two cartridges storing different substances (e.g., a cartridge that stores a drug or controlled substance, and a cartridge that stores a placebo). Optionally, a given cartridge may include two or more chambers, where a first chamber may store the controlled substance and a second chamber may store a placebo.

The placebo may be configured to have a similar taste, smell, and/or mouth feel as the controlled substance (e.g., opiate, psychotropic drug, or other drug declared by federal or state law to be illegal for sale or use, but that may be dispensed under a physician's prescription), and/or the placebo may be configured with flavoring that will both provide palatability to user, but also mask the taste of drug in order to achieve the desired placebo effect. If the controlled substance (drug or other active substance) has little taste when vaporized or nebulized, the controlled substance may have flavor added thereto (e.g., a desirable flavor, such as mango, strawberry, mint, watermelon, grape, punch, coffee, vanilla, ice cream, etc.) and the placebo may have the same or similar flavor added thereto so that the drug and the placebo may not be distinguishable by taste by the user.

The placebo may include water, vegetable glycerin (to act as a sweetener, preservative, and thickening agent), propylene glycol (which acts as a flavor carrier and preservative), flavoring, and/or an active ingredient (e.g., different than the controlled substance/drug, such as nicotine). Other or different ingredients may be used. The flavoring included in the placebo or controlled substance may be natural or artificial in nature.

For example, natural flavoring may comprise an essential oil, oleoresin, essence or extractive, protein hydrolysate, distillate, a product of roasting, heating or enzymolysis, which contains the flavoring constituents derived from a spice, fruit or fruit juice, vegetable or vegetable juice, edible yeast, herb, bark, bud, root, leaf or similar plant material, meat, seafood, poultry, eggs, dairy products, or fermentation products thereof. The artificial flavoring may include chemical flavoring from natural sources or artificial sources (e.g., synthetic chemicals). Synthetic chemicals may be preferred in certain instances as they may be more controlled, better safety tested, and less expensive.

As will be described, the substance dispensing device may be programmed to dispense, at a given moment in time, just the controlled substance, just the placebo, or a controlled combination of the controlled substance (dispensed from one cartridge) and the placebo (dispensed from a different cartridge). Use of the placebo and associated placebo effect may significantly aid the user in psychologically detoxifying from the drug/controlled substance and in curbing drug cravings. However, for certain drug intake control programs, no placebo is used. For certain drug intake control programs (e.g., methadone maintenance programs), the amount of controlled substance dispensed is not tapered, but is not permitted to exceed a certain threshold per time period and/or per puff.

By way of example, each time a patient inhales on the substance dispensing device, the substance dispensing device may dispense or withhold the drug/controlled substance based on a drug delivery program programmed into the substance dispensing device or other device that controls the substance dispensing device. Optionally, the substance dispensing device will be configured not to report or a provide a human perceptible indication to the patient as to whether a particular inhalation includes the drug or not. This technique may be utilized in aiding the user in psychologically detoxifying from the drug/controlled substance given the efficacy of the placebo effect.

Where both a drug/controlled substance cartridge and a placebo/flavor cartridge are being used and the patient is being weaned of the controlled drug/substance, as the amount/volume of the drug/controlled substance being dispensed is decreased, the amount/volume of placebo being dispensed may optionally be correspondingly increased (e.g., on a per puff basis) in order to compensate for the reduction in the drug/controlled substance being dispensed and to achieve the same mouth feel. This process may prevent the user from detecting when the drug/controlled substance is being withheld or the amount being dispensed reduced to enhance a detoxification process.

As noted above, the amount/volume of the drug/controlled substance being dispensed by the substance dispensing device may be gradually tapered. Such a gradual tapering program may be particularly helpful in detoxification with respect to certain substances, such as opiates, that are particularly difficult to wean an addicted patient off of. Cold-turkey detoxification, where an addict is immediately cut-off from the substance the addict is addicted to, can cause major health complications or death. Utilization of the devices, systems, and processes described herein may be utilized to provide safe, effective, and gradual detoxification without requiring an inpatient setting, and may reduce patient non-compliance.

However, for certain controlled substances (e.g., methadone), it may be advantageous to have a patient on a controlled maintenance dosage for an extended period of time (even for the remainder of the patient's life) to compensate for structural neurological changes that can occur with opiate/opioid addiction, where such structural neurological changes may make it more likely that a patient will relapse.

An authorized entity, such as a physician or addiction specialist, may be enabled to remotely administer and alter the drug delivery program and/or taper schedule as desired. For example, where the drug/controlled substance is a prescribed pain medication, the physician may be provided a user interface (e.g., via an application hosted on a physician device or via a user interface accessed from a web server via a browser) via which the physician can remotely increase or decrease the dosage and/or increase or decrease the frequency of the dosage as needed for pain.

Optionally, the user/patient may be periodically tested (e.g., by the physician or other specialist) to determine whether the user/patient is in compliance with a prescribed detoxification program. If the user/patient is determined not to be in compliance with the prescribed detoxification program (e.g., the user/patient is consuming a narcotic using a different delivery mechanism), the authorized entity may alter the detoxification program and/or disable the substance dispensing device.

Optionally, the substance dispensing device may be wirelessly or logically paired with or utilized in conjunction with a real time blood monitoring device to monitor drug saturation in patient's blood stream and to detect if the saturation level is above a threshold that indicates non-compliance with a detoxification program. Optionally, in response to detecting that the blood saturation is above a threshold (e.g., indicating that the saturation level is out of baseline for the programmed dose and/or that the patient is at risk of an overdose), the substance dispensing device may be commanded to dispense a substance (e.g., to counteract the drug and/or the drug effects of non-compliant usage). For example, if the drug is an opiate/opioid, naloxone or other opioid antagonist may be dispensed from a separate cartridge or cartridge chamber to counteract the effects of non-compliant use of the drug. By way of further example, if the drug comprises nicotine, a nicotine antagonist, such as Chantix, may be dispensed to counteract the non-compliant consumption of nicotine.

Optionally, the amount of drug antagonist dispensed may be based on the amount of the drug detected in the patient's bloodstream or body. For example, if the amount of opioid detected is between a first threshold and a second threshold, (indicating that the patient has exceed the current prescribed/ scheduled amount of consumption, but is not at risk of an overdose), a first amount of opioid antagonist may be dispensed. If, on the other hand, the amount of opioid detected exceeds a second threshold, indicating the patient is likely undergoing an overdose or is at risk of an overdose, a second, larger amount of opioid antagonist may be dispensed to reverse the overdose or risk of overdose. The presence and/or amount of a substance is a patient's blood stream may be detected using a sensor, such as a surface-enhanced Raman spectroscopy (SERS) sensor.

As discussed above, the substance dispensing device may be paired (e.g., wirelessly paired) with and/or communicate with a remote device, such as a smart phone (via an application installed on the device, such as a substance dispensing programming application). Optionally, in order for the substance dispensing device to be enabled to dispense a substance stored in a cartridge, a user needs to be authenticated via the remote device. For example, the user may be authenticated using biometric authentication provided via the remote device (e.g., facial recognition, fingerprint recognition, voice recognition, and/or the like). In addition or instead, a user may be required to enter a code (e.g., a password, a PIN, and/or the like) via an interface on the remote device. Optionally, if the substance dispensing device is not connected to the paired remote device, the substance dispensing device may inhibit the dispensation of a substance (e.g., a controlled substance and/or any cartridge substance). In response to the user being authenticated via the remote device, the remote device may transmit an encrypted enable command to the substance dispensing device, thereby enabling the substance dispensing device to dispense the controlled substance. Optionally, use of the substance dispensing device may be completely disabled so that even a placebo substance will not be dispensed from a placebo cartridge or chamber.

Optionally, if the substance dispensing device needs to be paired to a new device (e.g., because the current paired remote device is lost, no longer functioning, or has been traded in for the new device, such as a new smart phone), the user may be required to bring the new device and the substance dispensing device to an authorized entity (e.g., a treating physician or addiction specialist) to have the pairing with the new device performed.

Optionally, in response to the substance dispensing device detecting an attempted pairing with an unauthorized/unapproved remote device (e.g., an authorized smart phone), the substance dispensing device may automatically inhibit the dispensation of a substance and/or undergo a complete lockdown so that it will not accept any further pairing attempts.

Certain example substance dispensing devices, cartridges, and processes will now be described with reference to the figures.

Referring to FIG. 1, a substance dispensing device 102 may be cylindrical or rectangular in shape (although other shapes may be used). An air inlet may be located at one end of the substance dispensing device 102, and an outlet may be located at the other end of the substance dispensing device 102. Optionally, one or more air inlets and/or outlets may be located on one or more of the elongated sides of the substance dispensing device 102. Optionally, in addition or instead, air inlets and/or outlets may be provided on the cartridge.

As illustrated, the substance dispensing device 102 may be configured to receive one or more cartridges 302. The cartridges may be rectangular, oval, or other shape. Battery charging contact may be provided on an end of the substance dispensing device 102 or on one or more elongated sides of the substance dispensing device 102. For example, the substance dispensing device 102 may be configured to be received by an AC/DC convertor charging station or other charging station. Optionally, the substance dispensing device 102 may include an induction coil to enable wireless charging. Optionally, each cartridge receiving area may be configured with a "key" so that only certain types of cartridge configured to mate with the key may be fully inserted. For example, one cartridge receiving area may be configured to receive a first type of cartridge (e.g., a cartridge containing a vaporizable placebo) and not a second type of cartridge (e.g., a cartridge containing a vaporizable controlled substance), where the first type of cartridge has a different key mate, than the second type of cartridge. For example, a key may be plastic or other material having a protrusion configured to mate with a bore or other protrusion receiving structure on a cartridge.

Figure 2:
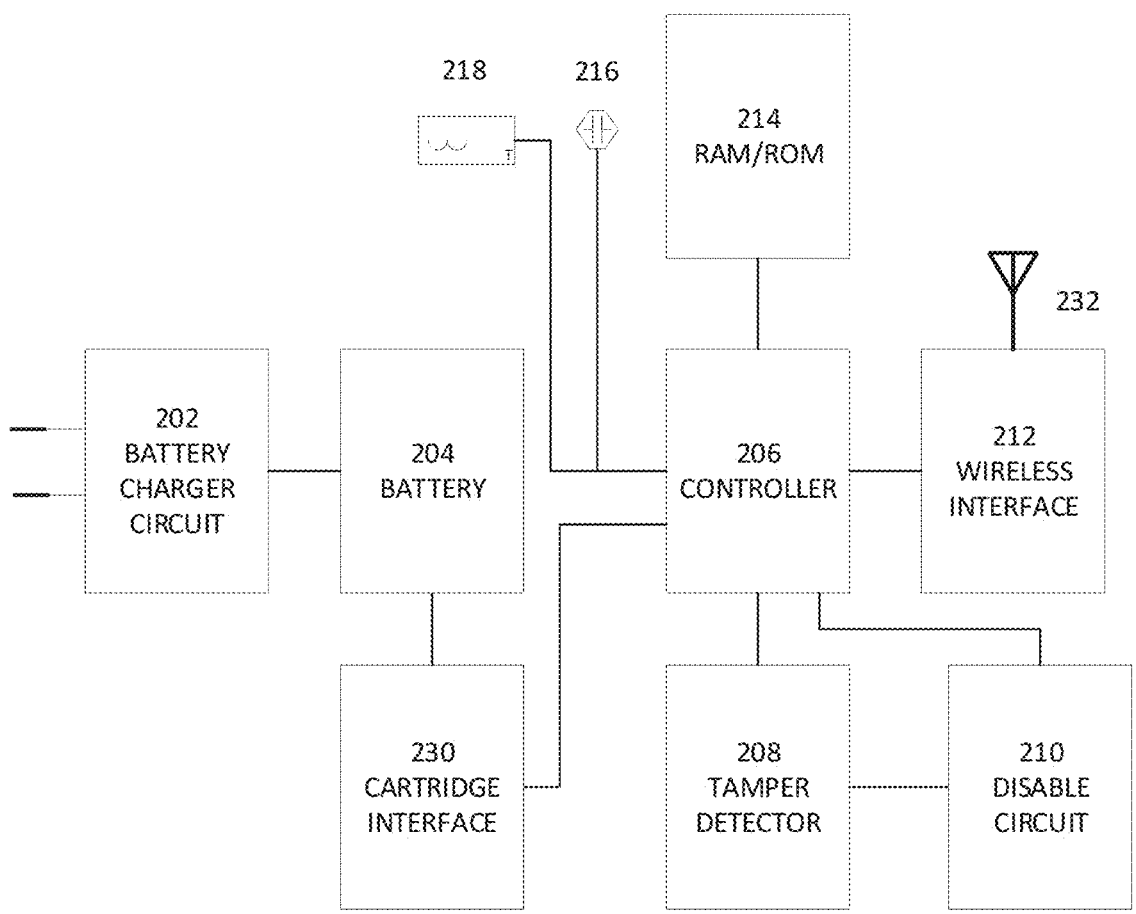
FIG. 2 illustrates an example architecture of a substance dispensing device.

Referring now to FIG. 2, an example substance dispensing device architecture is illustrated. The substance dispensing device includes, with a substance dispensing device body, a battery charging/protection circuit 202 (which may include charging contacts), a rechargeable battery 204 (e.g., a lithium-ion polymer battery or other battery technology that does not unduly suffer from memory effect), a controller device (e.g., a microcontroller or other processing device) 206, long term storage memory configured to store program instructions and working memory 214 (e.g., RAM, ROM, EEPROM, etc., which may be internal to or external to the controller device 206), an inhalation sensor 216 configured to sense a user's puffing action such as by detecting negative pressure or airflow (which when detected may activate resistive cartridge heating elements), one or more temperature sensors 218 (e.g., to sense the temperature of heating elements, the temperature of vaporized cartridge substances, ambient temperature, etc.), and a cartridge interface 230 (which may include cartridge interface contacts).

The cartridge interface 230 may communicate power from the battery 204 to one or more cartridges (e.g., to power heating elements and/or electronics included in the cartridges) coupled to the substance dispensing device. The cartridge interface 230 may be configured to enable the controller device 206 to read information from the cartridges (e.g., an indication regarding the cartridge contents, manufacturing date, lot number, a cartridge expiration date, a patient identifier, cartridge serial number, and/or a substance dispensing device unique identifier). The cartridge interface 230 may be configured to enable the controller device 206 to transmit commands to the cartridges, such as a content destruction command which causes a given cartridge to take an action to destroy (e.g., render inert) the substance stored by a given cartridge (e.g., by dispensing a controlled substance antagonist).

Optionally, the battery 204 may include multiple batteries. Optionally, where there are multiple batteries, one or more batteries may be reserved for use in anti-tamper processes. For example, as will be described in greater detail elsewhere herein, a battery may be dedicated to detecting tampering, and to a self-destruct or other disabling process (executed via the controller 206) that may be executed in response to detecting (by a tamper detector 208 discussed below) that someone is attempting to tamper with the substance dispensing device (e.g., by prying, bending or drilling an outer covering/shell of the substance dispensing device) and/or an installed cartridge. The battery dedicated to the self-destruct or other disabling process may also be charged by the battery charger circuit 202.

In order to ensure that the dedicated battery is charged in the event the self-destruct or other disabling process needs to be executed, the corresponding circuitry may be passive, in that only a closed circuit (e.g., caused by prying, bending or drilling an outer covering/shell of the substance dispensing device) actually powers the circuitry, to inhibit the discharge of the dedicated battery.

Optionally, instead of a dedicated battery, a portion of a battery 204 capacity may be reserved for use by the tamper detection and/or self-destruct processes and may not be used for vaporization/nebulization of substances for inhalation by a user. Another portion of the battery 204 capacity may be used by the substance dispensing device for vaporization/nebulization of substances for inhalation by a user. Thus, when the portion of the capacity that may be utilized by the substance dispensing device for vaporization/nebulization of substances for inhalation by a user is determined via a batter charge level detector (e.g., a Coulomb counter or battery fuel gauge) to be fully depleted/discharged, the circuit for vaporization/nebulization of substances may be disabled until the battery is sufficiently charged, thereby ensuring that there is sufficient battery capacity remaining to execute the tamper detection and/or self-destruct/disabling processes.

A wireless interface 212 (e.g., a cellular modem, a WiFi interface, a peer-to-peer interface, a Bluetooth interface, a low power interface, such as Bluetooth Low-Energy, Zig-Bee, Z-Wave, or 6LoWPAN interface) and one or more antennas 232 may be used to communicate with remote devices such as a patient's or medical service provider's smart phone, with a cloud based system, or other system.

A tamper detector 208 may include physical tampering or software hacking of the substance dispensing device. For example, the tamper detector 208 may be configured to detect a DNS rebinding attack, a denial service attack, or attempted insertions of malware by monitoring the content and/or source of data packets being transmitted to and/or from the substance dispensing device and/or to a device (e.g., a smart phone) having an application thereon configured to manage the substance dispensing device. By way of further example, the substance dispensing device may include an internal conductor (e.g., a relatively fragile conductive tape or trace) through which a current flows, wherein the tamper detector 208 may detect the presence of absence of such current flow. The tamper detector 208 may infer that someone is tampering with the substance dispensing device if it is determined that no current is flowing though the conductor (which may indicate that the conductor has been broken as a result of physical tampering).

By way of yet further example, someone prying, bending or drilling an outer covering/shell having a conductive material, such as a conductive, metallic mesh (e.g., connected to a positive or negative/ground terminal of a power source), may cause the mesh to contact an inner conductive layer (e.g., connected to the opposite power terminal as the conductive mesh), thereby closing a circuit and allowing current to flow between the mesh and the inner conductive layer. The tamper detector 208 may detect the closing of the circuit (e.g., by detecting a current flow through the circuit), and may initiate a self-destruct/disabling process (e.g., using the controller 206 and/or disable circuit 210), such as described elsewhere herein.

A disable circuit 210 may be configured to disable one or more functions/circuits of the substance dispensing device in response to the tamper detector 208 detecting tampering with the substance dispensing device or in response to the controller 206 receiving a remote disable command via the wireless interface 212 (e.g., from a medical service provider system).

As discussed elsewhere herein, the substance dispensing device may include a heating component, including heating elements and/or a heating chamber (not shown), or some or all of the heating component may be included in a cartridge.

If the substance dispensing device is to nebulize substances stored in cartridges, the substance dispensing device may store and/or dispense oxygen or compressed air, or may include a ultrasonic generator or mesh nebulizer to break up the substances to form small aerosol droplets that can be inhaled from the substance dispensing device. Thus, when nebulization is to be performed, optionally, the heating component may be replaced by a nebulizer component using one or more of the foregoing nebulization structures. Optionally, nebulization may be utilized instead of vaporization, where vaporization may denature a substance being dispensed (e.g., as a result of the heat that needs to be applied).

Figure 7:
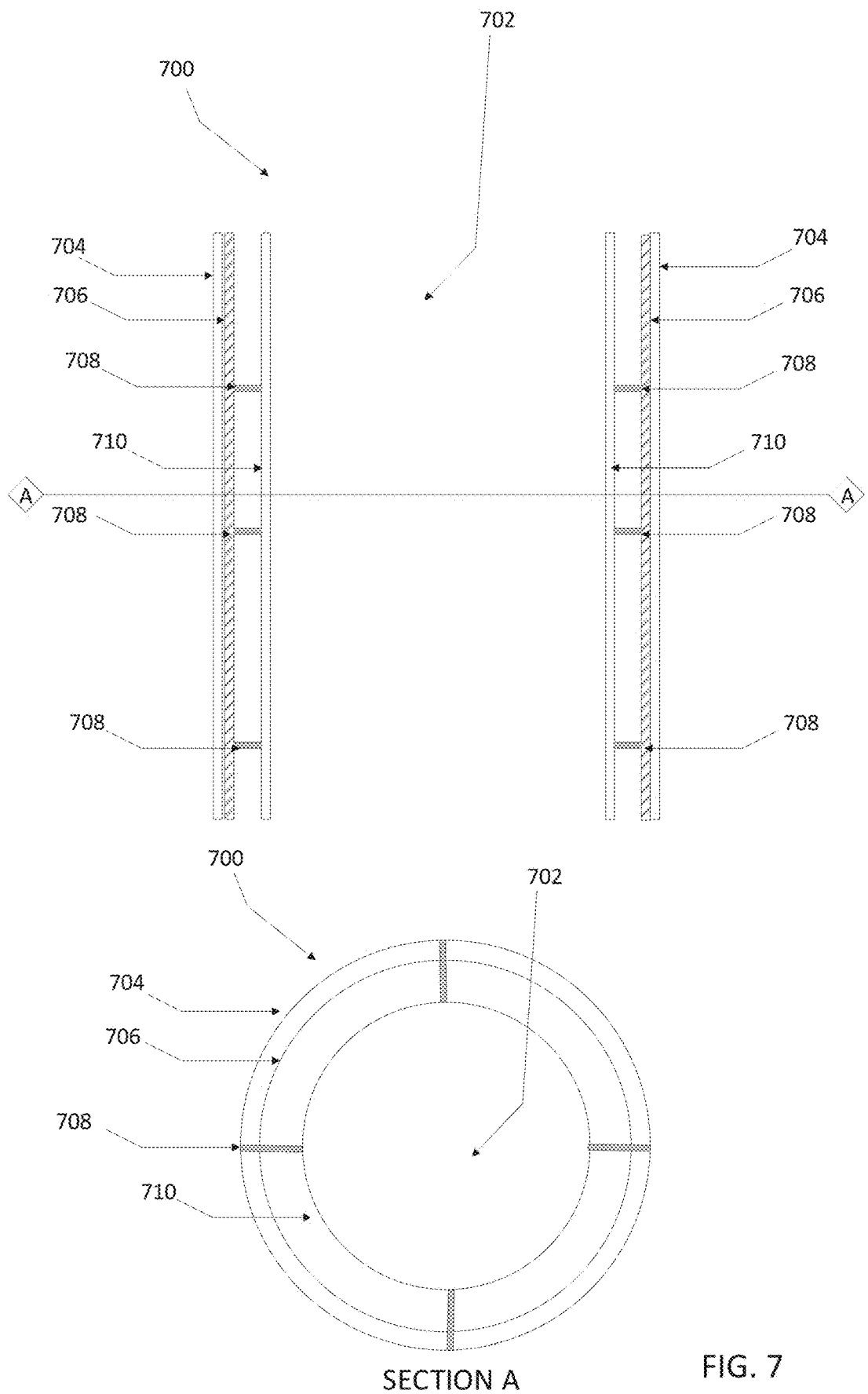
FIG. 7 illustrates example aspects of a substance dispensing device tamper detection structure.

FIG. 7 illustrates an example substance dispensing device 700 having a tamper detection structure. The central portion 702 of the substance dispensing device 700 may include chambers, vapor passageways, other structures, and/or circuitry, as discussed elsewhere herein. A flexible outer wall 704 may be provided. The outer wall 704, for example, may be thin aluminum (e.g., configured to bend or buckle under a force of 70-200 psi), a polymer, cardboard, or other material that may sufficiently bend of buckle under a threshold amount of force that indicates that someone may be trying to improperly access internal components of the substance dispensing device 700. The outer wall 704 may be rigid or strong enough not to flex or buckle under normal handling. The outer wall 704 may be of electrically conductive material (e.g., metal) and/or the inner side of the wall may be coated or lined with a conductive material, such as a metallic mesh 706. The outer wall or metallic mesh 706 may be connected to a first power source terminal (e.g., a positive voltage terminal). An inner wall 710 may likewise be metallic or have on outside coated or lined with an electrically conductive material which may be connected a second power source terminal (e.g., a negative voltage terminal or ground line). The inner wall 710 may be separated from the outer wall 704 by a collapsible scaffolding 708 or other structure.

When the outer wall 704 is unduly tampered with (e.g., by prying, bending or drilling), the outer wall 704 will flex or buckle so that it breaks or compresses the collapsible scaffolding 708 and comes in contact with the conductive side of the inner wall 710, thereby closing a circuit. The tamper detector may detect the closing of the circuit and initiate the self-destruct/disabling process.

Optionally, a sleeve (e.g., a non-conductive flexible or rigid sleeve), such as a plastic sleeve may surround the outer wall, to prevent the outer wall from being inadvertently flexed or buckled by normal handling.

Figure 3:
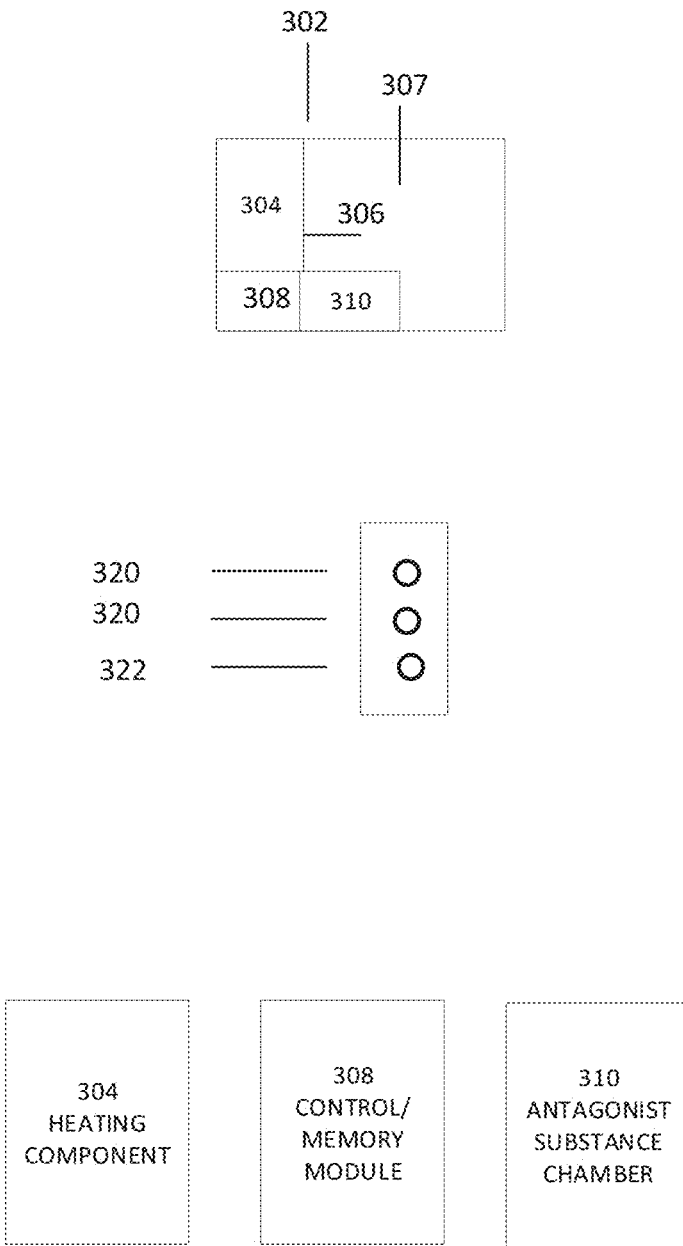
FIG. 3 illustrates an example cartridge.

FIG. 3 illustrates various example aspects of a cartridge 302, which may optionally include tamper resistant features and/or features that prevent unauthorized access to the contents of the cartridge. The cartridge 302 may include a heating component 304, a wick 306, circuitry 308, a substance chamber 307 (e.g., configured to store a substance, such as a controlled substance), and/or an optional substance chamber 310 (e.g., configured to store an antagonist or other substance configured to render the substance stored in chamber 307 inert or to counteract the effects of the substance stored in the substance chamber 307). Optionally, if the cartridge 302 is configured to store and dispense a placebo (and not a controlled substance), the cartridge 302 may not include a substance chamber 310. Thus, the substance dispensing device may be configured to receive cartridges having different physical structures and/or electronic components. The cartridge chambers may be preloaded with substances in chamber 307 or chamber 310 (e.g., by a physician or other authorized service provider) and provided to the user/patient to avoid the user/patient having unregulated access to the controlled substance. Optionally, the cartridge 302 may not include provisions to be refilled with a controlled substance and/or placebo by the user/patient.

The cartridge 302 may be formed from plastic (e.g., injected molded plastic). The exterior and/or any interior walls of the cartridge 302 may be clear in order to enable the visual inspection of the cartridge 302 contents. The walls of the substance chamber 310 interior to the cartridge 302 may be configured to be easily broken in response to any deformation of the cartridge 302, such as deformation that may result from someone attempting to tamper with the cartridge 302 (e.g., someone tampering to improperly extract the controlled substance from the chamber 307). Thus, if someone attempts to manipulate or otherwise physically tamper with the cartridge 302 (e.g., by twisting the cartridge, by apply more than a certain amount of pressure on a cartridge wall, etc.), a wall of the chamber 310 configured to be fragile may break or an orifice may otherwise be provided to chamber 310, and the substance stored in chamber 310 may be released into the substance chamber 307 to render the contents of substance chamber 307 inert. For example, one or more score/fracture lines may be formed on one or more walls, wherein the walls are configured to fracture along the score lines. The score lines may be formed by cutting partway through the walls (e.g., using a heated scoring tool), or may be formed via a molding process so that the walls are significantly thinner (e.g., 50%-80% thinner) than the thickness of the wall adjacent to the score lines.

The heating component 304 may include a heater/evaporating chamber, a substance wick, and/or a heating element (e.g., a ceramic coil comprising metal and ceramic). For example, the substance wick may be configured to contact/be immersed at least partly in a vaporizable substance stored in chamber 307, and draw the vaporizable substance towards or to the heating element. By including the heating component 304 within the cartridge 302, it may make it more difficult to tamper with the cartridge 302 to extract cartridge contents and may reduce the possibility of the contents leaking.

The circuitry 308 may optionally include a memory element storing one or more items of data (e.g., an indication regarding the cartridge contents, manufacturing date, lot number, a cartridge expiration date, a patient identifier, cartridge serial number, and/or a substance dispensing device unique identifier) that may be read by a controller device in the substance dispensing device. In addition, the circuitry 308 may optionally include an interface configured to receive commands from the controller device in the substance dispensing device (e.g., a command to release the contents of the substance chamber 310 into the substance stored in chamber 306). The circuitry 308 may include one or more sensors (e.g., temperature sensors configured to detect the temperatures of substances being vaporized in the cartridge 302).

The cartridge 302 may include contacts 320 configured to receive power from a battery in the substance dispensing device. The power may be used to power the heating elements in the heating component 304 and the circuitry 308. In addition, the cartridge 302 may include one or more contacts 322 configured to receive commands and/or transmit data to the controller device in the substance dispensing device.

Optionally, the cartridge 302 may include an air inlet orifice and/or outlet orifice via which air may be pulled in and pushed out as a user puffs the substance dispensing device, where the air may flow through the heating chamber and may be used as a carrier of the vaporized substance to the user. A pressure sensor may optionally be provided to detect when a user is puffing on the substance dispensing device or cartridge 302, wherein in response to detecting a puff, power from the batter may be routed to the heating elements to power the elements to vaporize the substance stored in chamber 306.

Figure 4:
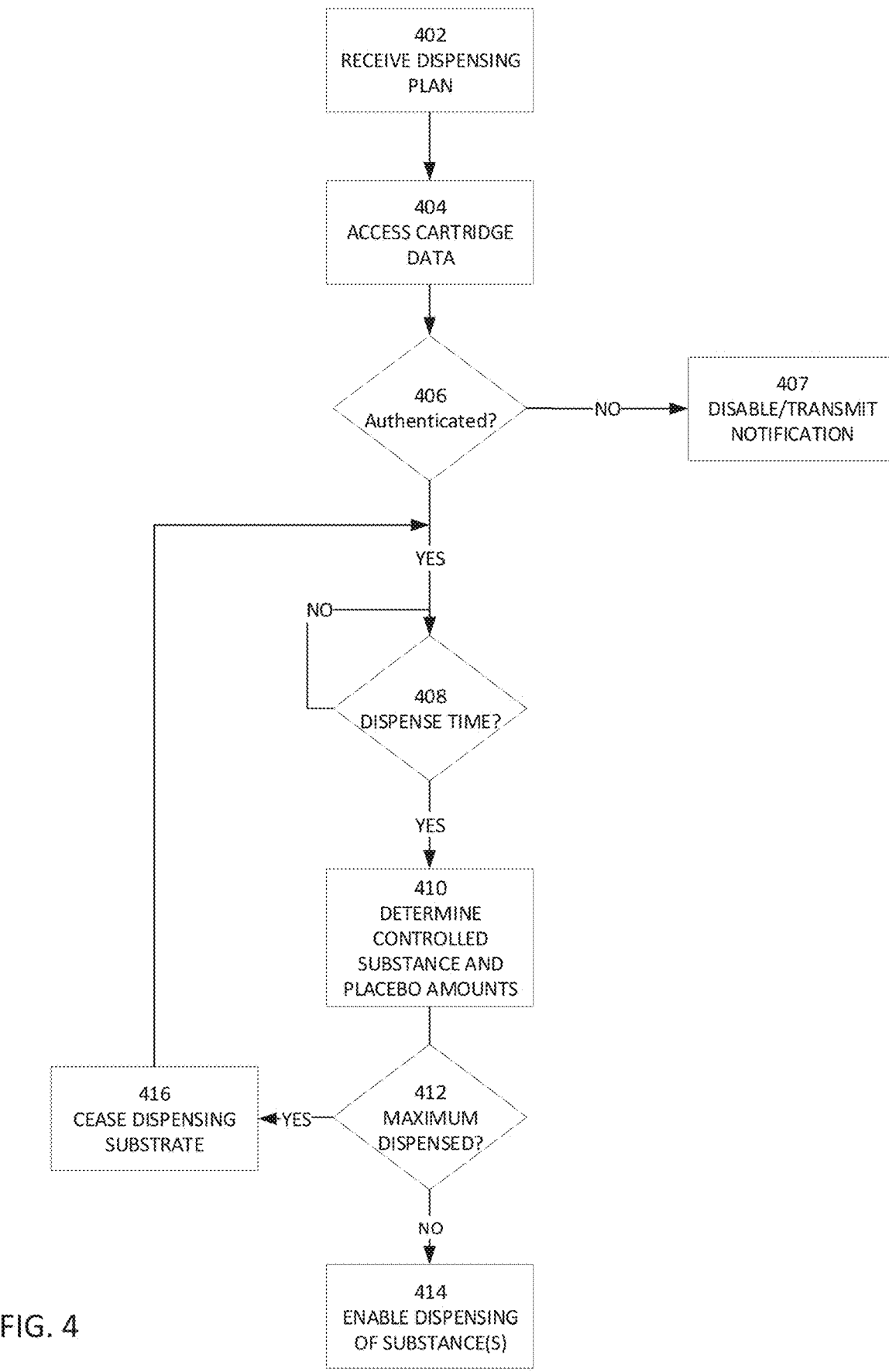
FIG. 4 illustrates an example process for operating an example substance dispensing device.

FIG. 4 illustrates an example process for dispensing substances. In this example, a controlled substance and/or a placebo may be dispensed according to a schedule or algorithm. The schedule or algorithm may specify a total volume amount to be dispensed over a specified time period and/or a rate at which the substance is to be dispensed. The amount of a substance dispensed may be monitored, and if the amount of substance dispensed is about equal to the specified total volume amount during a corresponding time period, the substance may cease dispensing the substance until the next time period begins. For example, infrared sensors, dual mode sensors, pressure sensors, and/or capacitive sensors positioned in or on an exterior wall of the cartridge may be used to sense the amount or volume of substance remaining in the cartridge. The amount of substance dispensed may also be determined using a substance detection sensor which may continuously monitor that amount of substance being inhaled by the user/patient, where the sensor may be positioned in the outlet or in a chamber leading to the outlet.

The amount remaining in the cartridge may be periodically measured. The current amount of the substance remaining may be subtracted from the amount remaining at the beginning of the current time period to determine the amount of the substance dispensed/consumed during the current time period.

At block 402, a substance dispensing plan may be received and stored in memory (e.g., substance dispensing device memory). For example, the substance dispensing plan may comprise an indication of how much of a controlled substance is to be dispensed and how much of a placebo is to be dispensed at a given point in time or within a time range (e.g., within a specified hour, 6 hour span, 12 hour span, 24 hour span, etc.). By way of example, over a period of time (e.g., days, weeks, months) the amount of controlled substance to be dispensed may be decreased and the amount of placebo to be dispensed may be increased to minimize a user's ability to detect the reduction of the controlled substance being dispensed. Optionally, in addition to or instead of a calendar schedule, an algorithm may be provided that calculates, at a given point in time, how much controlled substance and/or placebo is to be dispensed at a given point in time. The substance dispensing plan or algorithm may be received (wirelessly or via a wired connection) by the substance dispensing device from an administrator system (e.g., a physician, an addiction specialist, or other unauthorized person), such as an administrator smart phone or cloud based system. The substance dispensing plan scheduling rules may be periodically accessed by the substance dispensing device controller in response to the substance dispensing device inhalation sensor detecting a user puff on the substance dispensing device.

At block 404, the substance dispensing device may optionally access data from one or more cartridges installed in the substance dispensing device. For example, the accessed data may include an indication regarding the cartridge contents, the cartridge manufacturing date, the cartridge lot number, the cartridge expiration date, a cartridge expiration date, a patient identifier associated with the user for whom the cartridge was prescribed, a cartridge serial number, and/or a substance dispensing device unique identifier (indicating that the cartridge is only to be used with the substance dispensing device corresponding to the identifier).

At block 406, some or all of the cartridge data may be utilized to authenticate the cartridge and/or determine if the cartridge contents are permitted to be dispensed by the substance dispensing device and/or for the user. For example, the substance dispensing device may determine if the dispensing device unique identifier accessed from the cartridge matches the dispensing device unique identifier stored in computer readable memory of the dispensing device, and if a match is found the cartridge may be authenticated. By way of further example, the substance dispensing device may determine if the patient identifier matches the patient identifier stored in computer readable memory of the dispensing device or read from a remote patient/user device, and if a match is found the cartridge may be authenticated. In addition, optionally the cartridge expiration date may be compared to a current date (e.g., read from a local clock or received via a wireless interface from a remote source), to determine if the current date is after the cartridge expiration date (indicating that the cartridge has expired).

If the cartridge fails authentication and/or if the cartridge is determined to have expired, at block 407, the dispensing of the substance stored in the cartridge may be disabled, optionally the substance stored in the cartridge may be rendered inert (as described elsewhere herein), and/or a failure to authenticate or expiration notification may be generated and transmitted to one or more destinations (e.g., a patient device and/or a remote administrator device). Optionally, the substance dispensing device may be temporarily or permanently disabled.

If the cartridge is authenticated and has not expired, at block 408, the current date and time may be accessed and compared to the dispensing schedule specified by the dispensing plan. If the current date and time corresponds to a dispensing time specified by the dispensing schedule, at block 410 the amount of each substance stored in the substance dispensing device cartridges to be dispensed is determined from the dispensing plan. For example, a certain amount of a controlled substance stored in a first cartridge to be dispensed and a certain amount of a placebo stored in a second cartridge to be dispensed may be determined.

At block 412, a determination is made as to whether the maximum amount of scheduled substance has been dispensed for the current time period. For example, the process may detect the amount of substrate dispensed within the current time from sensor data and compare that amount with the maximum amount scheduled for the current time period. If the amount of substrate dispensed within the current time from sensor data is less than the maximum amount scheduled for the current time period then the maximum has not been reached.

If the maximum amount of scheduled substance has not been dispensed for the current time period, at block 414 the substance dispensing device is enabled to dispense the determined amount of each substance. The substance dispensing device may actually only dispense the substances in response to the user/patient puffing on the substance dispensing device.

If, at block 412, a determination is made that the maximum amount of scheduled substance has been dispensed for the current time period, then the process may cease dispensing the substance(s) until the beginning of the next time period.

Figure 5:
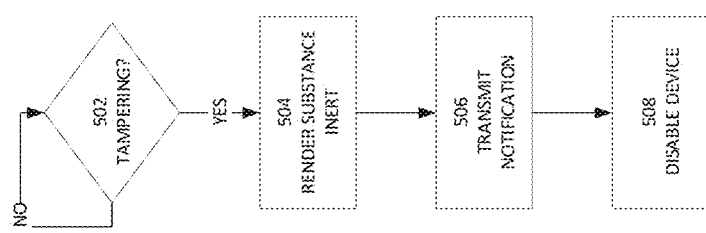
FIG. 5 illustrates an example tamper detection management process.

FIG. 5 illustrates an example process for detecting and managing tampering. At block 502, one or more forms of tampering are monitored via physical and/or software tamper sensors. For example, sensors may detect tampering of the substance dispensing device (e.g., physical tampering, software tampering, improper attempts to pair the substance dispensing device with an unauthorized device, etc.) and/or tampering of one or more cartridges (e.g., a controlled substance cartridge and/or a placebo cartridge).

In response to one or more forms of detected tampering, the process may perform one or more of the following remedial actions and/or other remedial actions. At block 504, the substances stored in one or more cartridges and/or chambers may be rendered inert (e.g., a controlled substance and/or placebo substance). For example, a substance antagonist, carbon, and/or other inert-rendering material may be dispensed into the substance to be rendered inert. The material may optionally be stored in a chamber within the cartridge that stores the substance to be rendered inert. For example, the chamber may include a solenoid controller valve which opens the chamber to enable the material to disperse into the substance to be rendered inert. For example, a controller in the substance dispensing device may command the valve to open in response to detected tampering. By way of further example, the valve may open in response to more than a threshold amount of pressure being applied to a wall or sealant of the cartridge.

At block 506, in response to tampering, the substance dispensing device may generate and transmit a wireless notification (e.g., a short text notification, email, peer-to-peer communication) via one or more wireless interfaces to one or more destinations. For example, the tampering notification may be transmitted to the user/patient device, to an electronic address or device associated with an authorized administrator, to a cloud-based system, and/or the like.

At block 508, in response to tampering, the substance dispensing device may be partially or wholly disabled, and he disabling may be temporary or permanent. For example, the substance dispensing device may be disabled so as to prevent the substance dispensing device battery from powering a heating element in the substance dispensing device and/or in one or more of the cartridges. Optionally, the substance dispensing device may be disabled so as to prevent the substance dispensing device controller from operating at all and/or to prevent the substance dispensing device from powering up (e.g., using one or more fuses). Optionally, the substance dispensing device may be re-enabled using an authorized administrator device.

Figure 6:
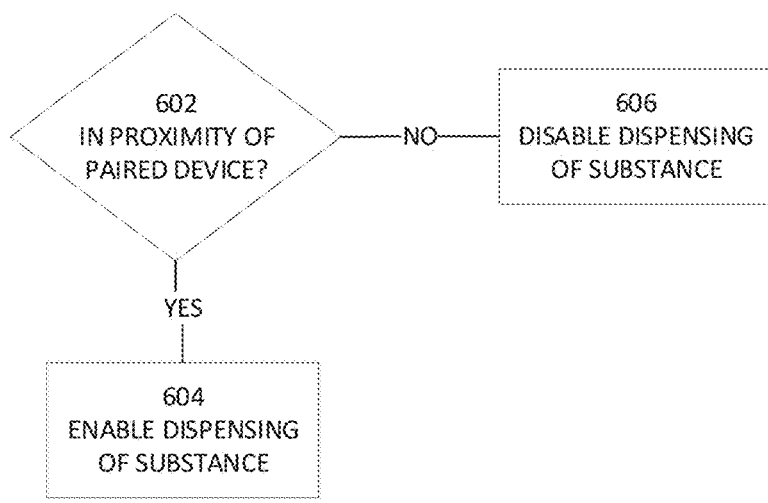
FIG. 6 illustrates an example proximity detection process.

FIG. 6 illustrates an example process for enabling a substance dispensing device to dispense one or more substances stored in one or more cartridges based on a proximity to at least one other device. For example, in order to enable dispensing of a substance from one or more cartridges or chambers, the substance dispensing device may need to be in physical proximity with an authorized device in wireless communication with the substance dispensing device. The authorized device may be a dedicated device (e.g., a keychain fob), a smart phone, an access point, or other device configured to enable proximity to be determined. For example, the authorized device may have been previously paired with the substance dispensing device (e.g., by an authorized administrator).

By way of example, the substance dispensing device may monitor the authorized device's signal using a sensor that measures a Received Signal Strength Indication from the authorized device, and if the signal strength falls below a certain level (e.g., −60 dBm, −80 dBm, etc.), the substance dispensing device may disable dispensing of one or more substances. For example, the substance dispensing device may disable dispensing of a controlled substance while still permitting dispensing of a placebo. Optionally, the sensitivity may be controlled by an authorized administrator (e.g., based on how the user/patient typically carries the phone, such as in a pocket, a purse, a backpack, or a purse). Optionally, the authorized device is paired with the substance dispensing device. The wireless communication may be via WiFi, WiFi Direct, Bluetooth, NFC, or otherwise.

At block 602, a determination is made as to whether the substance dispensing device is about within a certain distance of an authorized device (e.g., using a Received Signal Strength Indication). If the substance dispensing device is determined to be about within a threshold distance of an authorized device, at block 604, the substance dispensing device may be enabled to dispense (e.g., via vaporization or nebulization) one or more substances. If it is not determined that the substance dispensing device is within a threshold distance of an authorized device (e.g., because the authorized device is outside of the threshold distance, because the authorized device is off, or because the authorized device's signal is being blocked), at block 606 the substance dispensing device may inhibit dispensing of one or more substances.

Thus, as discussed herein, methods and systems are described that enable the controlled, dispensing of substances, such as controlled substances and placebos. In response to detecting tampering of a substance dispensing device and/or a substance container (e.g., a cartridge) the substance dispensing device may be disabled and/or a substance stored in a substance container may be rendered inert. Methods and systems are described that enable a detoxification plan and/or a controlled substance maintenance plan to be implemented.

The methods and processes described herein may have fewer or additional steps or states and the steps or states may be performed in a different order. Not all steps or states need to be reached. The methods and processes described herein may be embodied in, and fully or partially automated via, software code modules executed by one or more general purpose computers. The code modules may be stored in any type of computer-readable medium or other computer storage device. Some or all of the methods may alternatively be embodied in whole or in part in specialized computer hardware. The systems described herein may optionally include displays, user input devices (e.g., touchscreen, keyboard, mouse, voice recognition, etc.), network interfaces, etc.

The results of the disclosed methods may be stored in any type of computer data repository, such as relational databases and flat file systems that use volatile and/or non-volatile memory (e.g., magnetic disk storage, optical storage, EEPROM and/or solid state RAM).

The various illustrative logical blocks, modules, routines, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "may," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

While the phrase "click" may be used with respect to a user selecting a control, menu selection, or the like, other user inputs may be used, such as voice commands, text entry, gestures, etc. User inputs may, by way of example, be provided via an interface, such as via text fields, wherein a user enters text, and/or via a menu selection (e.g., a drop down menu, a list or other arrangement via which the user can check via a check box or otherwise make a selection or selections, a group of individually selectable icons, etc.). When the user provides an input or activates a control, a corresponding computing system may perform the corresponding operation. Some or all of the data, inputs and instructions provided by a user may optionally be stored in a system data store (e.g., a database), from which the system may access and retrieve such data, inputs, and instructions. The notifications/alerts and user interfaces described herein may be provided via a Web page, a dedicated or non-dedicated phone application, computer application, a short messaging service message (e.g., SMS, MMS, etc.), instant messaging, email, push notification, audibly, a pop-up interface, and/or otherwise.

The user terminals described herein may be in the form of a mobile communication device (e.g., a cell phone), laptop, tablet computer, interactive television, game console, media streaming device, head-wearable display, networked watch, etc. The user terminals may optionally include displays, user input devices (e.g., touchscreen, keyboard, mouse, voice recognition, etc.), network interfaces, etc.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. An electronic personal vaporizer system, comprising:
a first receiving area configured to removably receive a first cartridge including a vaporizable controlled substance;

a second receiving area configured to removably receive a second cartridge including a vaporizable placebo substance;
an inhalation sensor;
a rechargeable battery;
a network interface configured to be powered by the rechargeable battery;
at least one computing device configured to be powered by the rechargeable battery;
computer readable memory including instructions operable to be executed by the at least one computing device to perform a set of actions, configuring the at least one computing device to at least:
store dispensing plan scheduling rules for the vaporizable controlled substance and the vaporizable placebo substance in the computer readable memory;
at least partly in response to the inhalation sensor detecting a user inhalation, access the dispensing plan scheduling rules for:
the vaporizable controlled substance, and
the vaporizable placebo substance;
access current date and current time data;
access vaporizable controlled substance dispensing-related data for a first historical time period;
based at least in part on:
the dispensing plan scheduling rules for the vaporizable controlled substance and the vaporizable placebo substance,
the accessed current date and current time data, and
the vaporizable controlled substance dispensing-related data for the first historical time period,
cause:
a first amount of the vaporizable controlled substance to be dispensed from the first cartridge,
a second amount of the vaporizable placebo substance to be dispensed from the second cartridge;
detect software hacking comprising at least one of:
a DNS rebinding attack,
a denial of service attack, or
attempted insertions of malware;
receive a first wireless signal from a first device;
determine a signal strength of the first wireless signal from the first device;
at least partly in response to determining that signal strength of the wireless signal from the first device is below a first signal strength threshold inhibit dispensation of at least the vaporizable controlled substance from the first cartridge; and
a tamper detector assembly configured to enable detection of tampering of the first electronic personal vaporizer system,
the tamper detector assembly comprising:
an electrically conductive mesh;
a wall displaced from the electrically conductive mesh, wherein the wall is electrically conductive; and
a collapsible or compressible structure positioned between the electrically conductive mesh and the wall, wherein the collapsible or compressible structure is configured to enable the electrically conductive mesh to come into electrical contact with the wall in response to at least a threshold force in the range of 70 psi to 200 psi being applied to the electrically conductive mesh or wall.

2. The electronic personal vaporizer system as defined in claim 1, wherein:
the vaporizable controlled substance comprises a psychotropic drug and a first flavoring substance; and
the vaporizable placebo substance comprises glycerin and the first flavoring substance.

3. The electronic personal vaporizer system as defined in claim 1, further comprising:
a first set of conductive contacts disposed in the first receiving area, the first set of conductive contacts configured to convey power to the first cartridge; and
a second set of conductive contacts disposed in the first receiving area, the second set of conductive contacts configured to convey power to the second cartridge.

4. The electronic personal vaporizer system as defined in claim 1, the electronic personal vaporizer system-configured to:
at least partly in response to electronically detecting, using the tamper detector, physical tampering of the electronic personal vaporizer system,
inhibit vaporization of the vaporizable controlled substance.

5. The electronic personal vaporizer system as defined in claim 1, further comprising:
a tamper detector assembly configured to enable detection of tampering of the first electronic personal vaporizer system,
the tamper detector assembly comprising:
a first wall configured to buckle under a force of at least 200 psi,
the tamper detector configured to detect when the first wall has buckled.

6. The electronic personal vaporizer system as defined in claim 1, the electronic personal vaporizer system-configured to:
at least partly in response to electronically detecting, using the tamper detector, physical tampering of the electronic personal vaporizer system, issue a command to an interface of the first cartridge to release a substance within the first cartridge configured to render the vaporizable controlled substance inert.

7. The electronic personal vaporizer system as defined in claim 1, the electronic personal vaporizer system-configured to:
at least partly in response to electronically detecting, using the tamper detector, physical tampering of the electronic personal vaporizer system, cause a substance to be released within the first cartridge configured to render the vaporizable controlled substance inert.

8. The electronic personal vaporizer system as defined in claim 1, further comprising: the first cartridge, the first cartridge configured with at least a first wall separating a first chamber and a second chamber, wherein the first chamber is configured to store the vaporizable controlled substance and the second chamber is configured to store an antagonist of the vaporizable controlled substance, wherein the first wall is scored with one or more score line so as to fracture along at least one score line in response to a first amount of pressure being applied to at least a first portion of the first cartridge.

9. The electronic personal vaporizer system as defined in claim 1, further comprising a nebulizer.

10. A computer-implemented method executed using a substance dispensing system comprising:
under control of a hardware computing device configured with specific computer-executable instructions:
receiving dispensing plan scheduling rules for a vaporizable or nebulizable controlled substance to be dispensed by the substance dispensing system;

storing the dispensing plan scheduling rules for the vaporizable or nebulizable controlled substance in computer readable memory;
detecting, using an inhalation sensor, a user inhalation;
at least partly in response to the inhalation sensor detecting the user inhalation, accessing the dispensing plan scheduling rules for the vaporizable or nebulizable controlled substance;
accessing current date and current time data;
based at least in part on:
  the dispensing plan scheduling rules for the vaporizable or nebulizable controlled substance, and
  the accessed current date and current time data,
enabling:
  a first amount of the vaporizable or nebulizable controlled substance to be dispensed from a first reservoir,
  a second amount of a vaporizable or nebulizable placebo substance to be dispensed from a second reservoir;
detecting software hacking comprising at least one of:
  a DNS rebinding attack,
  a denial of service attack, or
  attempted insertions of malware;
receiving a first wireless signal from a first device;
determining a signal strength of the first wireless signal from the first device; and
  at least partly in response to determining that signal strength of the wireless signal from the first device is below a first signal strength threshold inhibit dispensation of at least the vaporizable or nebulizable controlled substance from the first reservoir; and
detecting physical tampering of the substance dispensing system using a tamper detector assembly of the substance dispensing system,
the tamper detector assembly comprising:
an electrically conductive mesh;
a wall displaced from the electrically conductive mesh, wherein the second wall is electrically conductive; and
  a collapsible or compressible structure positioned between the electrically conductive mesh and the wall, wherein the collapsible or compressible structure is configured to enable the electrically conductive mesh to come into electrical contact with the wall in response to at least a threshold force in the range of 70 psi to 200 psi being applied to the electrically conductive mesh or wall.

11. The computer-implemented method as defined in claim 10, the method further comprising:
at least partly in response to electronically detecting tampering of the substance dispensing system, issuing a command to an interface of the first reservoir to release a substance within the first reservoir configured to render the vaporizable or nebulizable controlled substance inert.

12. The computer-implemented method as defined in claim 10, the method further comprising:
electronically detecting when a first wall of the substance dispensing system comes into contact with a second wall of the substance dispensing system; and
at least partly in response to detecting that the first wall of the substance dispensing system has come into contact with the second wall of the substance dispensing system, inhibiting vaporization or nebulization of the vaporizable or nebulizable controlled substance.

13. The computer-implemented method as defined in claim 10, wherein:
the vaporizable or nebulizable controlled substance comprises a psychotropic drug and a first flavoring; and
the vaporizable or nebulizable placebo substance comprises glycerin and the first flavoring.

14. The computer-implemented method as defined in claim 10, wherein:
enabling:
  the first amount of the vaporizable or nebulizable controlled substance to be dispensed from the first reservoir, and
  the second amount of a vaporizable or nebulizable placebo substance to be dispensed from the second reservoir,
further comprises:
  powering at least one reservoir heating element.

15. The computer-implemented method as defined in claim 10, the method further comprising:
at least partly in response to electrically detecting physical tampering of the substance dispensing system:
inhibiting vaporization or nebulization of the vaporizable or nebulizable controlled substance.

16. The computer-implemented method as defined in claim 10, the method further comprising:
at least partly in response to electrically detecting physical tampering of the substance dispensing system substance dispensing system, enabling a substance to be released within the first reservoir configured to render the vaporizable or nebulizable controlled substance inert.

17. The computer-implemented method as defined in claim 10, the method further comprising:
transmitting vaporizable or nebulizable controlled substance dispensing data to a remote system.

18. The computer-implemented method as defined in claim 10, the method further comprising:
detecting that an overdose of the vaporizable or nebulizable controlled substance may have occurred; and
at least partly in response to detecting that an overdose of the vaporizable or nebulizable controlled substance may have occurred, causing an antagonist to the vaporizable or nebulizable controlled substance to be dispensed to the user.

19. A non-transitory computer-readable storage medium storing computer-executable instructions that when executed by a processor cause the processor to perform operations comprising:
receiving a dispensing plan for a vaporizable or nebulizable controlled substance;
storing the dispensing plan for the vaporizable or nebulizable controlled substance in computer readable memory;
detecting, using a substance dispensing apparatus inhalation sensor, a user inhalation;
at least partly in response to the inhalation sensor detecting the user inhalation, accessing the dispensing plan for the vaporizable or nebulizable controlled substance;
accessing current date and current time data;
based at least in part on:
  the dispensing plan for the vaporizable or nebulizable controlled substance, and,
  the accessed current date and current time data,
enabling:
  a first amount of the vaporizable or nebulizable controlled substance to be dispensed from a first reservoir, a second amount of a vaporizable or nebulizable placebo substance to be dispensed from a second reservoir;
detecting software hacking comprising at least one of:
a DNS rebinding attack,
a denial of service attack, or
attempted insertions of malware;
receiving a first wireless signal from a first device;
determining a signal strength of the first wireless signal from the first device;
at least partly in response to determining that signal strength of the wireless signal from the first device is below a first signal strength threshold inhibit dispensation of at least the vaporizable or nebulizable controlled substance from the first reservoir;
detecting physical tampering of the substance dispensing apparatus using a tamper detector assembly of the substance dispensing apparatus,
the tamper detector assembly comprising:
an electrically conductive mesh;
a wall displaced from the electrically conductive mesh, wherein the second wall is electrically conductive; and
a collapsible or compressible structure positioned between the electrically conductive mesh and the wall, wherein the collapsible or compressible structure is configured to enable the electrically conductive mesh to come into electrical contact with the wall in response to at least a threshold force in the range of 70 psi to 200 psi being applied to the electrically conductive mesh or wall.

20. The non-transitory computer-readable storage medium as defined in claim 19, the operations further comprising:
at least partly in response to electronically detecting tampering of the substance dispensing apparatus, issuing a command to an interface of the first reservoir to release a substance within the first reservoir configured to render the vaporizable or nebulizable controlled substance inert.

21. The non-transitory computer-readable storage medium as defined in claim 19, the operations further comprising:
detecting when a first wall of the substance dispensing apparatus comes into contact with a second wall of the substance dispensing apparatus; and
at least partly in response to detecting that the first wall of the substance dispensing apparatus has come into contact with the second wall of the substance dispensing apparatus, inhibiting vaporization or nebulization of the vaporizable or nebulizable controlled substance.

22. The non-transitory computer-readable storage medium as defined in claim 19, wherein:
enabling:
the first amount of the vaporizable or nebulizable controlled substance to be dispensed from the first reservoir, and
the second amount of the vaporizable or nebulizable placebo substance to be dispensed from the second reservoir,
further comprises:
powering at least one reservoir heating element.

23. The non-transitory computer-readable storage medium as defined in claim 19:
at least partly in response to electronically detecting physical tampering of the substance dispensing apparatus:
inhibiting vaporization or nebulization of the vaporizable or nebulizable controlled substance.

24. The non-transitory computer-readable storage medium as defined in claim 19:
at least partly in response to detecting physical tampering of the substance dispensing apparatus, enabling a substance to be released within the first reservoir configured to render the vaporizable or nebulizable controlled substance inert.

25. The non-transitory computer-readable storage medium as defined in claim 19, wherein the substance dispensing apparatus inhalation sensor comprises a negative pressure and/or an airflow sensor.

26. The non-transitory computer-readable storage medium as defined in claim 19, the operations further comprising:
transmitting controlled substance dispensing data to a remote system.

* * * * *

UNITED STATES PATENT AND TRADEMARK OFFICE
CERTIFICATE OF CORRECTION

| | | |
|---|---|---|
| PATENT NO. | : 11,793,949 B2 | Page 1 of 1 |
| APPLICATION NO. | : 16/927639 | |
| DATED | : October 24, 2023 | |
| INVENTOR(S) | : Jesse David Adelaar | |

It is certified that error appears in the above-identified patent and that said Letters Patent is hereby corrected as shown below:

In the Specification

On Column 5, Line 34: Delete "server" and insert -- server. --.

In the Claims

On Column 22, Line 26: In Claim 16, after "the" delete "substance dispensing system".

Signed and Sealed this
Twenty-sixth Day of December, 2023

*Katherine Kelly Vidal*

Katherine Kelly Vidal
*Director of the United States Patent and Trademark Office*